United States Patent
Parekh et al.

(10) Patent No.: US 6,835,374 B2
(45) Date of Patent: Dec. 28, 2004

(54) ANTIPERSPIRANT/DEODORANT ACTIVE FOR NO WHITE RESIDUE STICKS AND SOFT SOLIDS

(75) Inventors: Jawahar C. Parekh, Livingston, NJ (US); Pradip T. Amin, Edison, NJ (US)

(73) Assignee: Reheis, Inc., Berkeley Heights, NJ (US)

( * ) Notice: Subject to any disclaimer, the term of this patent is extended or adjusted under 35 U.S.C. 154(b) by 246 days.

(21) Appl. No.: 10/278,673

(22) Filed: Oct. 23, 2002

(65) Prior Publication Data

US 2004/0081632 A1 Apr. 29, 2004

(51) Int. Cl.⁷ .................. A61K 7/32; A61K 7/34; A61K 7/38; A61K 7/00
(52) U.S. Cl. .................. 424/65; 424/66; 424/68; 424/400; 424/401
(58) Field of Search .................. 424/65, 66, 68, 424/400, 401

(56) References Cited

U.S. PATENT DOCUMENTS

| | | |
|---|---|---|
| 3,405,153 A | 10/1968 | Jones |
| 3,420,932 A | 1/1969 | Jones |
| 3,472,929 A | 10/1969 | Jones |
| 3,507,896 A | 4/1970 | Jones |
| 3,523,130 A | 8/1970 | Jones |
| 3,555,146 A | 1/1971 | Jones |
| 3,792,070 A | 2/1974 | Jones |
| 4,089,120 A | 5/1978 | Kozischek |
| 4,147,766 A | 4/1979 | Kozischek |
| 4,154,816 A | 5/1979 | Roehl et al. |
| 4,518,582 A | 5/1985 | Schamper |
| 4,719,102 A | 1/1988 | Randhawa |
| 4,720,381 A | 1/1988 | Schamper |
| 4,722,835 A | 2/1988 | Schamper |
| 4,724,139 A | 2/1988 | Palinczar |
| 4,725,430 A | 2/1988 | Schamper |
| 4,743,444 A | 5/1988 | McCall |
| 4,781,917 A | 11/1988 | Luebbe |
| 4,816,261 A | 3/1989 | Luebbe |
| 4,987,243 A | 1/1991 | Kawam |
| 5,098,698 A | 3/1992 | Kawam |
| 5,258,174 A | 11/1993 | Schebece |
| 5,292,530 A | 3/1994 | McCrea |
| 5,376,363 A | 12/1994 | Benfatto |
| 5,429,816 A | 7/1995 | Hofrichter |
| 5,449,511 A | 9/1995 | Coe |
| 5,463,098 A | 10/1995 | Giovanniello |
| 5,492,691 A | 2/1996 | Bahr et al. |
| 5,547,661 A | 8/1996 | Sun et al. |
| 5,549,887 A | 8/1996 | Galleguillos |
| 5,718,876 A | 2/1998 | Parekh |
| 5,725,836 A | 3/1998 | Rouanet |
| 5,864,923 A | 2/1999 | Rouanet |

FOREIGN PATENT DOCUMENTS

| | | |
|---|---|---|
| EP | 0792634 A2 | 9/1997 |
| EP | 1057474 A1 | 12/2000 |
| WO | WO9518599 | 7/1995 |
| WO | WO00/97768 A2 | 12/2001 |

*Primary Examiner*—Shelley A. Dodson
(74) *Attorney, Agent, or Firm*—Arthur J. Plantamura

(57) ABSTRACT

Antiperspirant actives that produce practically no visible white residue, even against a black background is provided by the reduction of the particle size, using a refractive index modifier, to a point where the antiperspirant active on application provides no discernible whiteness.

When formulated into an antiperspirant stick, the antiperspirant actives produce an improved combination of functional properties, including excellent antiperspirancy, smooth skin feel, nontacky, quick drying and leave no visible residue.

The exceptionally high surface area of the antiperspirant active results in rapid and efficient delivery of the active to the sweat glands and possible absorption. The absence or reduced quantity of suspending and flow enhancing agents, of gellant and surfactant, is believed to improve the antiperspirant active's ability to physically reach the sweat glands and improve efficacy.

32 Claims, No Drawings

ANTIPERSPIRANT/DEODORANT ACTIVE FOR NO WHITE RESIDUE STICKS AND SOFT SOLIDS

This invention relates to efficacious antiperspirant characterized by a property that renders invisible or transparent residue which remains on the skin. More particularly, the invention provides a highly efficacious concentrated antiperspirant system which when formulated into a conventional antiperspirant formulation and applied to the skin does not give unsightly white residue on the skin and clothing. The reduced residue effect of the antiperspirant product may be in the form of a stick, soft solid, suspension, roll-ons or spray, etc. The reduced residue or low residue means the product on application to the skin provides no discernible whiteness or visible residue.

BACKGROUND OF INVENTION

The antiperspirant and deodorant market offers a wide diversity of products. The physical forms of antiperspirants vary greatly. They include aerosols, pump sprays, squeeze sprays, creams, roll-ons, suspension roll-ons, deodorant sticks, clear gels, soft solids, etc. First and foremost in the hierarchy of consumer needs is long lasting control of odor and wetness. Consumers also want their antiperspirants to have excellent sensory properties on application and certain aesthetics. The preferred form of antiperspirant in USA is the stick application due to their high efficacy and good application properties.

Antiperspirants (except aerosols and sprays) are applied to an area of the body such as the axilla by rubbing to deposit a layer of antiperspirant. Accordingly, it is desirable that the ingredients used in any antiperspirant formulation result in an antiperspirant which is smooth, non-greasy, feel warm, quick drying, non tacky and leaves no visible residue. One of the disadvantages that exist with many stick formulations is that a white chalky residue is often left on the body and transferred to clothing. Since the use of dark-colored garments has increased among consumers, women in particular are dissatisfied with white residue from personal care products including antiperspirant and deodorant on clothing. A chalky residue after use of an antiperspirant stick is due in part to the fact that relatively large particles of the antiperspirant salt are employed in stick antiperspirants. Since the antiperspirant stick is white the deposit on the skin is also white.

In the early 1990's, clear products swept the consumer market place bringing everything from transparent dishwashing liquid to colorless colas. Although the popularity of these products has faded in some segments, product clarity remains a market force in the personal care industry. No where is a transparent product more sought after than in the antiperspirant stick market where consumers associate clarity with the lack of unsightly white residue on skin and clothing. This desire has prompted manufacturers of antiperspirant and deodorants to develop clear products. There are several apparent benefits associated with clear antiperspirant products. A clear product conveys a clean, pure and natural image; i.e., in an antiperspirant no visible product residue is left on skin or clothing. Consumer research rates clear products high on perception of superiority. The technology associated with clear stick and clear gel is specific and restricts the type of an antiperspirant active that can be used. Some of the important requirements for each of various antiperspirant forms are described below:

With respect to Clear Stick Antiperspirants:

The antiperspirant active must be stable in soluble and transparent form in the solvent system used; the solvent can be the same as that used to form the basic matrix for the gelling agent, or an alternative solvent.

An antiperspirant active that has already been pre-solubilised in a polyhydric alcohol, such as propylene glycol. This pre-solubilization ensures the formation of crystal clear compositions even in mixed glycol systems.

Use of enhanced efficacy aluminum zirconium actives is preferred to improve efficacy since the levels of use of the antiperspirant actives in clear sticks are markedly lower than in conventional solids. The comparative values are about 10–15% active level in clear sticks versus about 20–25% active level in opaque or translucent antiperspirant sticks.

Use of buffers to stabilize Di-benzaldehyde Monosorbitol Acetate (DBMSA) gelling agent or self buffered actives with higher pH than conventional antiperspirant actives.

The potential disadvantages with clear antiperspirant sticks include:

These products exhibit different application properties, particularly some stickiness after application and a less dry feel on the skin.

There is a potential for greater skin irritation due to the relatively high levels of glycolic fluids currently employed.

Clarity depends on the implementation and control of very precise manufacturing procedures at relatively high process temperatures and pHs. Also, antiperspirant salts themselves are weak oxidising agents, and under certain processing conditions may cause some degradation of glycols.

Shelf life stability frequently becomes difficult with clear sticks, and when they are unstable it becomes especially evident to the consumer. Unlike opaque products, clear sticks that begin to separate or cloud constitute a distinct and immediate turn-off for the consumer.

Lower clinical efficacy is generally acknowledged for this form of product, although they do conform to the Monograph requirement of a 20% sweat reduction in at least 50% of the test subjects. Lower efficacy is attributed to lower concentration of the active and higher pH of the active.

With respect to Clear Gel Antiperspirants:

Clear gel antiperspirant products offer several advantages. To illustrate, there is no product residue during or after application and a water-white clarity is achievable. High levels of enhanced efficacy actives can be used to deliver the expected levels of wetness protection. This is also a decided advantage compared to clear stick products.

There are several possible approaches to develop transparent formulations, such as the formation of gelled or thickened solutions, or the formation of micro-emulsions containing relatively high surfactant concentrations. Both of these approaches possess ingredient and production limitations.

A relatively simple and versatile third option is to form a water-in-oil emulsion in which the refractive indices of the continuous and dispersed phases are matched. This requires a precise control of the refractive index. The addition of a silicone surfactant such as dimethicone copolyol is desirable to achieve stability. Many formulations use a pre-blended combination of volatile silicone and dimethicone copolyol, also known as 'self-emulsifying volatile silicone', for ease of formulation.

Technically speaking, these emulsions are not microemulsions. The continuous or oil phase is typically a blend of liquids, and can include, for example, additives, such as, cyclomethicone, dimethicone, mineral oils, and various esters, as well as the silicone emulsifier.

The disperse or water phase typically includes one, or a combination of various polar species such as water, propylene glycol, sorbitol, glycerin, and ethanol, as well as the antiperspirant active.

To provide an optically clear gel, the refractive indices of the oil and water phase are adjusted as necessary to bring them within 0.0004 to 0.001 units at room temperature. Thus, the precise control of refractive index of an active and both the continuous and disperse phases is extremely important for this technology. Drawbacks to clear gels are that they suffer from becoming hazy when temperature changes or due to the evaporation of volatile ingredients like alcohol/silicone, causes an imbalance in the formulation. Efficacy of clear gel is also not as high as for opaque sticks and soft solids.

Reduced Residue Sticks

A solution to the consumer demand for an efficacious product with no residue is an opaque white stick with reduced residue or no residue. A number of patents have been issued for reduced residue sticks. However, there is a need for an active which when formulated into a solid gives no visible residue, has high efficacy, has silky feeling, has no tackiness and dries rapidly.

To achieve this objective two different approaches were investigated. Common to both approaches was the incorporation of an activated antiperspirant to improve efficacy whose refractive index has been modified by forming an adduct with a suitable organic solvent. The approach involved making a dense spherical particle to minimize surface area per unit mass while maintaining aesthetically acceptable application making use of sphericity of particles. The second approach was to reduce average particle size to about 1 micron, and further reduce refractive index of the active by enrobing it with a selected organic fluid which is dermatologically acceptable for topical application and facilitate particle size reduction during comminution.

The steps involved in preparing the novel composition of the invention comprise:

Preparing an inorganic-organic adduct of activated or nonactivated basic aluminum chlorides and comprise those having the formula $$Al_2(OH)_{6-x_1}Y_{x_1}(R)p \quad (1)$$

wherein Y is Cl, Br, I and/or $NO_3$ and $_{x1}$ is greater than zero and less than or equal to six (i.e., $0<x1\leq 6$); wherein "R" is an organic solvent having at least two carbon atoms and at least one hydroxy group and "p" has a value of from zero to 1.5;
and including reaction products of those of the above formula and zirconium compounds of the formula $$ZrO(OH)_{2-ab}X_b \quad (2)$$

wherein X is a member selected from the group consisting of halide, nitrate, perchlorate, carbonate or sulfate; b varies from 0.5 to 2; a is the valence of X; (2-ab) is greater than or equal to zero.

A particular group of such antiperspirant active includes various aluminum-zirconium-glycine salts with the formula:

$$Al_nZr(OH)_{(3n+4-x)}Y_x(AA)q(R)p \quad (3)$$

wherein "n" is about from 2.0 to 10.0; preferably from 3 to 8;
wherein "x" is from 1.4 to 12.3, calculated from metal to chloride ratio (M/Cl, 0.9:1–2.1:1); preferably from 2 to 8, wherein "Y" is Cl, Br, I and/or $NO_3$;
wherein AA is an amino acid, and "q" is from about 0.5 to 3.0, preferably from 1 to 2; and
wherein "R" is an organic solvent having at least two carbon atoms and at least one hydroxy group and "p" has a value of from zero to 1.5; and
aluminum or aluminum and zirconium complexes having metals/anion ratio of 0.9:1 to 2.1:1 where an anion could be Cl, Br, I and/or $NO_3$, with or without additives such as amino acids or polyhydric alcohols or combination thereof.

The invention contemplates also those antiperspirant actives comprising aluminum and aluminum zirconium salts combined with zinc and/or tin, i.e. Al/Zr/Zn, Al/Zn, Al/Sn, Al/Zr/Sn, and the like, actives.

The organic solvent which may be employed in preparing antiperspirant formulation of the invention may be selected from any of the suitable polyhydric alcohols, non-polyhydric alcohols and other suitable organic solvents which are generally used in cosmetic compositions and which are liquid at room temperature and preferably have refractive index (RI) less than 1.5. Thus, some organic solvents used in preparing adducts of basic aluminum chloride are propylene glycol (PG) RI 1.430, dipropylene glycol (DPG) RI 1.446, tripropylene glycol (TPG) RI 1.454, 2 methoxy ethanol RI 1.402, 1-methyl 2-propanol RI 1.403, 2 ethoxy ethanol RI 1.407, and 3 methoxy butanol RI 1.411 and silicone copolyols.

The process technology used for the preparation of an antiperspirant adduct comprise of mixing basic aluminum chloride as represented by the general formula.

$$Al_2(OH)_{6-x_1}Y_{x_1}$$

wherein Y is Cl, Br, I and/or $NO_3$ and $x_1$ is greater than zero and less than or equal to six (i.e. $0<x_1\leq 6$) is mixed with a suitable organic solvent such as propylene glycol, dipropylene glycol, tripropylene glycol or glycerin or a combination thereby at room temperature to about 105° C., may be refluxed for 30 minutes to about 4 hrs; is cooled to room temperature is either dried or mixed with zirconium hydroxy chloride glycinate solution having Cl/Zr atomic ratio of (0.8:1 to 2:1) and which has been refluxed for 2 hrs. The resultant solution is allowed to react at least for 30 minutes and is then filtered to obtain slightly amber to colorless solution. This solution is then dried by suitable conventional means (viz spray dryer, vacuum dryer, oven dryer, tray dryer, freeze dryer, etc.) to yield a homogeneous composition with the modified refractive index. The change in RI is a function of the organic solvent chosen, concentration of the solvent in the final product and drying method used and the amount of water associated with the adduct.

Organic solvent may be added to zirconium hydroxy glycinate solution before, during or after the refluxing step or it may be added after zirconium hydroxy glycinate solution has been added to basic aluminum chloride and just before the spray drying at room temperature or at temperature up to 100° C. Alternatively some of the organic solvent may be added to basic aluminum chloride and the remainder to zirconium hydroxy glycinate solution.

Refractive index of various basic aluminum chloride adducts and of aluminum zirconium glycine propylene glycol complex prepared in Reheis lab are shown in Table I.

TABLE I

| Sample # | Active | Organic Solvent | Refr. Index |
|---|---|---|---|
| 1 | Aluminum Chlorohydrate (ACH)* | — | 1.512 |
| 2 | ACH | DPG (20%) dipropylene glycol | 1.496 |
| 3 | ACH | DPG (20%) | 1.500 |
| 4 | ACH | TPG (20%) tripropylene glycol | 1.496 |
| 5 | ACH | PEG 400 (20%) polyethylene glycol | 1.506 |
| 6 | Aluminum Sesquichlorohydrate (RE301)* | DPG (20%) | 1.502 |
| 7 | RE301 | TPG (20%) | 1.498 |
| 8 | ACH | 2 Methyl 1,3 Propanediol | 1.506 |
| 9 | ACH | RE301 (31%) 2 Methyl 1,3 Propoanediol | 1.512 |
| 10 | ACH | 1,4 Butanediol | 1.504 |
| 11 | RE301 | 1,4 Butanediol (32%) | 1.510 |
| 12 | ACH | Methoxy Ethanol (32.3%) | 1.518 |
| 13 | RE301 | Methoxy Ethanol (32.3%) | 1.522 |
| 14 | ACH | Ethoxy Ethanol | 1.516 |
| 15 | RE301 | Ethoxy Ethanol (7.5%) | 1.516 |
| 16 | ACH | Ethoxy Ethanol (6.9%) | 1.516 |
| 17 | Al/Zr Tetrachlorohydrex (Rezal 36GP SUF)* | | 1.565 |
| 18 | Activated Al/Zr Tetrachloro-hydrex (Reach AZP-908)* | — | 1.572 |
| 19 | Activated Al/Zr Tetrachlorohydrex Glycine Propylene Glycol Complex (Reach AZP-908 PG)* | Propylene Glycol | 1.5364 |
| 20 | Macrospherical Al/Zr Tetrachlorohydrex Glycine Propylene Glycol Complex (Reach AZP-908 PGO)* | Propylene glycol | 1.5312 |

*Products of Reheis Inc.

The data in Table I show significant reduction in RI of aluminum zirconium tetrachlorohydrex glycine propylene glycol complex. The procedures described in U.S. Pat. Nos. 3,420,932; 3,405,153; 3,472,929; 7,507,896; 3,523,130; 3,555,146; 3,792,070 may be used alone or in combination with the technology used in U.S. Pat. No. 5,718,876 to form antiperspirant adducts in accordance with the present invention and as described in the present application. The relevant disclosure in these patents is incorporated herein by reference.

Various experiments were conducted to study the effect of metals to chloride ratio, the amount of bound water associated with the product, degree of polymerization, concentration of organic solvent in adducts and drying methods viz vacuum oven drying, freeze drying and spray drying. Basic aluminum chloride antiperspirant showed change in refractive index by ±0.01 to ±0.02. However, higher change in RI of Al/Zr complex was seen when an adduct was formed with an organic solvent such as propylene glycol and spray dried using the approach described in U.S. Pat. Nos. 4,089,120 and 4,147,766.

The Effect of Surface Area/Unit Mass on the Antiperspirant Actives

The advantage offered by the patented spray drying technology described in U.S. Pat. No. 4,089,120 is that perfectly spherical thick walled particles with high bulk density and a very narrow particle size distribution is obtained. Table II shows comparison of physical properties of regularly spray dried aluminum zirconium tetrachlorohydrex powder and micronized to superultrafine grade which is used almost universally in the manufacturing of efficacious suspensoid stick and macrospherical aluminum zirconium glycine propylene glycol tetrachlorohydrex complex. The reduced surface area per unit mass results into reduced number of particles/mass and results into less visible white residue.

TABLE II

| | REACH AZP-908* SUF | REACH AZP-908 PGO** |
|---|---|---|
| Scott Density, gm/in$^3$ | 5.92 | 10.82 |
| Tap Density, gm/cm$^3$ | 0.70 | 0.99 |
| Median Particle Diameter in Microns | 2.5–3.5 | 38 |
| Surface Area/Volume, m$^2$/cm$^3$ | 3.22 | 0.45 |
| Surface Area/Mass, m$^2$/gm | 1.57 | 0.26 |
| Refractive Index | 1.572 | 1.5312 |

$$\frac{\text{Surface Area of 908 PGO}}{\text{Surface Area of AZP 908 SUF}} = \frac{0.26}{1.57} \quad 83\% \text{ Reduction}$$

*Activated aluminum zirconium tetrachlorohydrex glycine complex a product of Reheis Inc.
**Macrospherical activated aluminum zirconium tetrachlorohydrex glycine, propylene glycol complex, a product of Reheis Inc.

The Hygroscopicity of Antiperspirant Actives

Since activated products tend to be more hygroscopic they have significantly lower critical humidity (equilibrium moisture) values than their corresponding unactivated form and they pick up moisture readily under ambient conditions. Thus, an activated salt's RI is lowered upon application more readily than of an unactivated salt and show less white residue.

Complexing an antiperspirant active with propylene glycol not only tends to lower the refractive index but also lowers critical humidity and makes the product very hygroscopic. (Equilibrium moisture was determined using the method described in a paper titled "Equilibrium Moisture Content of Antiperspirant System" published in Aerosol Age December 1974). This is highly beneficial as it further lowers RI upon application and thereby reduces visibility of the residue. The reduction in critical humidity or increase in hygroscopicity as the antiperspirant active is activated and further complexes with an organic moiety to form an adduct is shown by Table III.

TABLE III

| Active | Critical Humidity |
|---|---|
| 5/6 Basic Aluminum Chloride (ACH)* | 28% |
| Propylene Glycol Adduct of ACH (Rehydrol II)* | 4% |
| Unactivated Al/Zr Tetrachlorohydrex (Rezal 36GP)* | 26% |
| Activated Al/Zr Tetrachlorohydrex (Reach AZP-908)* | 18% |
| Propylene Glycol Adduct of Activated Al/Zr Tetrachlorohydrex (Reach AZP-908 PGO)* | 10% |
| Basic Aluminum Sesquichloride (Reach 301)* | 18% |
| Reach 301 Propylene Glycol Adduct of Basic Aluminum Sesquichloride (Reach 301 PGO)* | 11% |

*Products of Reheis Inc.

The Reduced Residue Stick Using Propylene Glycol Adduct of an Antiperspirant

An activated aluminum zirconium glycine propylene glycol salt (available from Reheis, Inc., as Reach AZP-908 PGO) having high density spherical particles with low surface area to mass ratio was formulated into an opaque stick using the formulation shown in Table IV and was compared in blind panel tests versus several well known marketed brands. Twenty-five male and female subjects with varying skin color received a controlled application of products on their forearms, and were then asked to rate the products for residue immediately and thirty minutes after application. The subjective rate scale with a five-point numerical scale with a score of 1 for "least residue" and 5 for "most residue". Representative results with REACH® AZP-908 PGO versus national brands are provided in Table IV. The data demonstrates that the reduced residue antiperspirant sticks prepared using polyol containing aluminum zirconium tetrachlorohydrex having high density spherical particles are consistently superior to the control commercial samples tested for perceived residue.

TABLE IV

| Ingredients | % By Wt. |
|---|---|
| A. REACH ® AZP-908 PGO (a) | 24.00 |
| B. Cyclomethicone (Pentamer) | 24.00 |
| C. Polydecene (Ethylflo 364-nF) (b) | 17.50 |
| D. Polyethylene AC-617-A © | 3.00 |
| E. Hydrogenated Castor Oil | 2.50 |
| F. Promyristyl PM-3 (d) | 5.00 |
| G. PEG-8 Distearate | 2.50 |
| H. Stearyl Alcohol | 19.00 |
| I. Talc, 325 Mesh | 1.00 |
| J. Cab-O-Sil M-5 (e) | 1.50 |
| K. Fragrance | q.s. |

Procedure

1. Add B and C to reaction vessel and heat to 75° C.
2. Add D and E sequentially and mix well after each addition. Cool to 70° C.
3. Add F, G and H sequentially, mixing well after each addition and maintaining 70° C.
4. Increase mixing and add A, maintaining 70° C.
5. Add I and J sequentially, mixing well after each addition.
6. Cool to 65° C. and add K.
7. Pour into stick casing at 65° C. and refrigerate 15–30 minutes.

TABLE V

| Product | Immediately After Application | 30 Minutes After Application |
|---|---|---|
| Reach ® AZP-908 PGO | 1.2 | 1.2 |
| Brand A | 2.5 | 2.2 |
| Brand B | 4.1 | 4.2 |
| Brand C | 4.1 | 4.4 |
| Brand D | 3.3 | 3.3 |

Another benefit derived from the use of these physically modified adducts is improved white color or reduced off white color when the product is viewed in the container. Antiperspirant sticks are more acceptable to consumers if they appear white as opposed to slightly yellowish, since the white color is often associated with quality and purity. Table VI demonstrates improvement in color of the stick when active is replaced by its propylene glycol adduct while using the same base.

TABLE VI

| Active | Measurement of Yellow Coloration ΔYB* |
|---|---|
| Superfine Unactivated Al/Zr Tetrachlorohydrex Glycine Complex (Rezal 36GP SUF*) | 10.82 |
| Superfine Activated Al/Zr Tetrachlorohydrex Glycine Complex (Reach AZP-908 SUF*) | 7.81 |
| Activated Al/Zr Tetrachlorohydrex Glycine Propylene Glycol Complex (Reach AZP-908 PG*) | 2.88 |
| Macrospherical Activated Al/Zr Tetrachlorohydrex Glycine Propylene Glycol Complex (Reach AZP-908PGO*) | 2.10 |

*ΔYB values were measured in a reflectance mode using Macbeth Color-Eye Model 2020 from Gretag Macbeth, NY.

When tested at an equivalent active concentration in a suspension roll-on formulation, using volar forearm, propylene glycol adduct of an activated salt showed enhanced efficacy when compared to nonactivated adduct and efficacy equivalent to an activated product. Results are shown by Table VII.

TABLE VII

| | % Sweat Reduction | | | |
|---|---|---|---|---|
| | Antiperspirant Active | | | |
| | Rezal ® 36 GP | Rezal ® 36 GPG* | Reach ® AZP-908 | Reach ® AZP-908 PG |
| Number of Panelists | 34 | 35 | 34 | 35 |
| Average ± Standard Deviation | 46.0 ± 3.6 | 45.6 ± 4.3 | 56.13 ± 4.29 | 55.9 ± 3.9 |
| Range | 39.6–53.0 | 39.3–53.9 | 45.8–65 | 48.8–64.7 |
| % Improvement | — | — | — | 22% |

*Al/Zr Tetrachlorohydrex glycine propylene glycol complex, a product of Reheis Inc.

This work established that an inorganic—organic adduct of basic aluminum chlorides and comprising those having the formulas 1, 2 and 3 when formulated into an antiperspirant stick gives significant reduction in white residue and shows significantly reduced color contribution to the stick while maintaining high efficacy.

SUMMARY OF THE INVENTION

A primary objective of the present invention is to improve formulations of the hereinabove referenced antiperspirant actives so that practically no white residue is visible even against a black background by the reduction of the particle size, using a refractive index modifier, to a point where the antiperspirant active essentially looses its ability to produce visible interference with the passage of light waves.

One factor which determines the optical appearance of a dispersion formulation is the particle size of antiperspirant and any other ingredients which may be present in the solid form. While the effect of particle size upon optical appearance has been investigated and described in the prior art its practical application in achieving the novel results in accordance with the invention have not been obvious therefrom. The ability of a particle of any given material to scatter or to diffuse light of particular wavelength is a function of its particle size relative to that wavelength. Various estimates have placed the most effective particle diameter for hiding power at approximately one half the wavelength of the light involved. Therefore, as the diameter of a particle becomes increasingly smaller than one half of the shortest wavelength of visible light, about 4000 angstroms for violet, it begins to disappear because it loses its ability to produce visible interference with the passage of light waves.

Since antiperspirant compositions require a very high concentration of active ingredients it has been estimated that the particle sizes to obtain optical clarity need not exceed about 0.20 micron and preferably 0.1 micron. It is also known that dry grinding of antiperspirant to this level is not economically practical or feasible.

Unfortunately, when such small particle sizes are used, other factors become important such as how to prevent such small particles from agglomerating to reform larger particles that could no longer be suited for clear colloidal dispersions.

Individual particles may be associated into agglomerates or aggregates. Particles in an agglomerate are only loosely associated while in an aggregate, the particles are held together strongly to form a ball or block that acts as distinct particles for all practical purposes.

A related problem often encountered in the manufacturing of stick antiperspirant is the settling of an active in the molten stick matrix during the cooling phase resulting in an uneven distribution of the active and hence its uneven performance during the use. To minimize or eliminate this problem, suspending agents such as talc or finely ground silica are used. However, silica and talc present dusting and health related problems and the finished products do not provide excellent skin feel as they tend to increase drag during its application, promote formation of gritty particles and increased residue.

Beside health concerns in handling of silica and talc the product also affects aesthetics of the finished stick; the product tends to have gritiness and leaves moderate white residue on the skin.

It accordingly is an object of this invention to provide an antiperspirant active composition which when formulated into an antiperspirant stick has an improved combination of functional properties, including excellent antiperspirancy, smooth skin feel, nontacky, quick drying and leave no visible residue.

It is another objective of the invention to make antiperspirant compositions which are self suspending and have a long settling time when diluted in antiperspirant formulations such as soft solids, sticks and as a result do not require the use of suspending agents. Such antiperspirant compositions are easier to process and because they omit suspending agents and powder flow enhancers like talc and silica, they avoid health related problems posed by these products from handling in a very fine powder form.

It is another objective of this invention to provide antiperspirant compositions which have an excellent smooth feel during application and have a dry feel after application.

It is a further objective of this invention to provide formulations of excellent antiperpsirancy. The very high surface area of the active results in rapid and efficient delivery of the active to the sweat glands and possible absorption. It is believed that absence or reduced quantity of suspending and flow enhancing agents and gellant and surfactant improves the antiperspirant active's ability to physically reach the sweat glands and improve efficacy.

Still a further objective of this invention is to provide a cost effective antiperspirant composition that affords the advantages of minimizing capital and processing cost for the antiperspirant and deodorant manufacturers;

The product can be transported within the manufacturing facility readily by a single pumping system for use in antiperspirant sticks, soft solids and other forms in any part of the world as opposed to an expensive pneumatic conveying system for highly hygroscopic finely micronized powder.

The product minimizes inventory and QC/QA cost as the number of ingredients to be stored and assayed are minimized.

The product affords easy technology transfer for a Global Manufacturer and simplifies implementation of uniform product quality between different plants.

It is still another objective of this invention to provide customized ready to use composition for antiperspirant and deodorant manufacturers such that during wet milling other ingredients may be readily incorporated to provide the desirable aesthetics; or enhanced deodorancy by including antimicrobials such as Triclosan, substituted glycerines; like ethyl hexyl glycerine; antioxidants like Vitamin E; fragrance, etc.

The formulations of the invention contemplate those antiperspirants covered by FDA OTC Tentative Final Monograph (Aug. 20, 1982) as Category I.

DETAILED DESCRIPTION OF THE INVENTION

The method of the present invention comprises the use of a plurality of steps to provide an antiperspirant composition which when formulated into an antiperspirant stick or soft solids formulation leaves no visible white residue. Included are the following four steps:

Preparation of an inorganic-organic adduct of an activated or unactivated antiperspirant comprising those represented by the formulas (1), (2) and (3) hereinabove defined and an organic solvent comprising mono and polyhydric alcohol and silicon copolyols which are generally used in cosmetic compositions and which are liquid at room temperature shown in Table VIII are some such suitable solvents and are useful in deriving the desired refractive index of the dried antiperspirant adduct of between about 1.450 and 1.580 and Drying the product such as by spray drying such that low surface area/mass ratio is achieved Suspending the powder in a non aqueous phase wherein the non aqueous phase consists of a nonwater miscible organic liquid comprising linear and branched hydrocarbons, polyesters and polyethers from fatty acids and alcohols, alkoxylated fatty esters of PEG and silicon copolyols and alkloxylated methyl glucoside and wherein the non aqueous organic components are selected so that the refractive index of the final liquid phase is about 1.4 to 1.5. Shown in Table IX are some of the acceptable ingredients for non aqueous phase Introducing the non aqueous suspension into comminution equipment to reduce the average particle size of the suspended particle to less than 3 microns and preferably less than one micron such that refractive index of the final non aqueous suspension has RI from 1.4000 to 1.4710 and has at least About 20% to 65% solids for most applications concentrations between 40% and 50% preferred.

The gel-like smooth suspension when prepared in accordance with the invention and properly formulated into an antiperspirant stick leaves no visible white residue when applied to a forearm. The absence of residue is confirmed by the measurement of chromaticity index as measured by Color Analyzing Instrument (Macbeth ColorEye Model 2020). The antiperspirant stick made using the novel antiperspirant active of this invention when applied on the black paper using three even strokes at an even pressure gave a chromocity index value below 0.4, no white residue was visible to a naked eye.

TABLE VIII

Mono and Polyhydric Alcohol Liquid at Room Temperature

| | |
|---|---|
| Propylene Glycol | Dipropylene Glycol |
| Tripropylene Glycol | 2-Methoxy Ethanol |
| 1-Methoxy 2-Propanol | 2-Ethoxy Ethanol |
| 3-Methoxy Butanol | 1,4-Butanediol |
| 2-Methyl, 1,3-Propanediol | Glycerin and Substituted Glycerin like ethyl hexyl glycerin |
| Silicon Copolyols | Diglycerol |

TABLE IX

Non Aqueous Phase Ingredients

Diisopropyl Adipate (Ceraphyl 230 - ISP Van Dyk Inc., Belleville, NJ 07109)
Glycereth-7 - Benzoate (Dermol G-76 - Alzo Inc., Sayerville, NJ 08872)
Phenyl Trimethicone (DC-556 - Dow Corning Corporation, Midland, MI 48686)
Phenyl Ethyl Dimethicone (Silsoft-PEDM - OSI Specialties Inc., Sistersville, WV 26175)
PPG-14-Butyl Ether (Ucon Fluid AP - Amerchol Corporation, Edison, NJ 08818)
PPG-15-Stearyl Ether Benzoate (Finsolv TPP - Finetex Inc., Elmwood Park, NJ 07407)
2-Phenyl Propyl terminate silicone oil (SF-1555 - General Electric Co., Waterford, NY 12188)
Lecithin (ADM Lecithin, Decatour, IL 62526)
Alkoxylated esters of PEG
    POE (20)* Sorbitan Mono Oleate (Tween-80 - ICI, New Castle, DE 19720)
    POE (20) Sorbitan Mono Laurate (Tween-20)
    POE (20) Sorbitan Mono Stearate (Tween-60)
    POE (20) Sorbitan Mono Palamitate (Tween-40)
Alkyl Polyglycoside (Plantaren 2000N - Henkel Corporation, Hoboken, NJ 07030)
Dimethicone (SF-1202 - GE Co., Waterford, NY 12188)
Dimethicone Copolyols (OSI Specialties, Inc., Sistersville, WV 26175)
Light Mineral Oil (OSI Specialties, Inc., Sistersville, WV 26175)

*Polyoxy ethylene products of ICI.

In accordance with the method of present invention an aqueous basic aluminum chlorides and comprise those having the formula

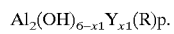

Wherein Y is Cl, Br, I and/or $NO_3$ and $x_1$ is greater than zero and less or equal to six (i.e. $0 < x_1 \leq 6$) wherein "R" is an organic solvent such as propylene glycol, dipropylene glycol, trirpropylene glycol, 2 methoxy ethanol, 2 ethoxy ethanol, 3 methoxy butanol and the like and the combination thereof having at least two carbon atoms and at least one hydroxy group, and "p" has a value of from zero to 1.5, is mixed at room temperature to about 105° C., may be refluxed from about 30 minutes to about 4 hrs; cooled to room temperature and mixed with zirconium hydroxy chloride glycinate solution having Cl/Zr atomic ratio of (0.8:1 to 2:1) and which has been refluxed for about 2 hrs. The resultant solution is allowed to react for at least 30 minutes and is then filtered to obtain a slightly amber to colorless solution. The second step involves spray drying of the solution and comprise those having the formulas 1, 2 and 3 using a porous metal disc for atomization as described in U.S. Pat. No. 4,089,120 (description incorporated in full herein) to yield a product having a homogeneous high density spherical particles and low surface area/mass ratio.

In the method of the invention, an organic solvent may be added to zirconium hydroxy glycinate solution before, during or after the refluxing step or it may be added after zirconium hydroxy glycinate solution has been added to basic aluminum chloride and just before the spray drying at room temperature or at temperature up to 100° C. Alternatively some of the organic solvent may be added to the basic aluminum chloride and the remainder to the zirconium hydroxy glycinate solution.

The third step involves suspension of the spray dried powder which consist of a non aqueous suspensions are characterized such that the non aqueous phase comprises a substantial nonpolar nonwater miscible organic liquid of linear and branched hydrocarbons, polyesters and polyethers from fatty acids and alcohol, alkoxylated fatty esters of PEG and silicone copolyols, having low surface tension and RI in the range of 1.400 to 1.470.

The proper selection of the ingredients for the non-aqueous phase is important; the criteria used in selecting the ingredients include:

Capable of coating antiperspirant particle uniformly to further lower its refractive index and/or modify its optical properties. Low surface tension and RI in the range of 1.400 to 1.470 are important.

Provides stearic structure to the non-aqueous phase, thus improving suspension characteristics of antiperspirant actives in the medium.

The property of imparting a dry feeling and better skin moisturization on application to an axillary area. Possesses the property to give a silky feeling when applied to the skin.

The fourth and final steps of this invention involves wet milling of the non aqueous suspensions to an average particle diameter of less than 3 micron and preferably less than one micron. Suitable milling equipment should have the capability of wet milling product under controlled temperature without contaminating the product with the grinding media and should be preferably amenable to a continuous operation. Media mill, for example, are ideally suited for this application. Another suitable equipment is the spinning tube in tube device (SST™) available from Holl Technologies Inc. Camarilla, Calif. Proper selection of a grinding mill, grinding media, etc. are important to achieve an average particle size not exceeding about three microns and preferably about one micron or less for the reasons detailed hereinabove. In connection with the examples described in the present application the media mill manufactured by Netzsch was used.

The composition and method of the invention will be further described in the examples which follow. It will be understood, however, that the invention is not to be limited to the details described therein, except as may be required by the appended claims. Parts specified use by weight unless otherwise indicated.

EXAMPLE I 16.5 kg of basic aluminum chloride solution (Al 11.26%; Cl 8.82%; Al:Cl atomic ratio of 1.67) was mixed with 5.2 kg of USP grade propylene glycol solution (99.5%) and the solution was refluxed for 2 hrs. with agitation. The solution was cooled down to room temperature. To 21.45 kg of this solution was slowly added 10.2 kg of zirconium hydroxy chloride glycinate solution at room temperature. (Zr 16.85%; Cl 7.9%; glycine 13.6%) which was refluxed for 2 hrs at 90° C. and spray dried. Aluminum zirconium tetrachlorohydrex glycine complex (Reach AZP-908 PG) powder (Al 12%, Zr 11.9%, Cl 14.7%, Glycine 11.5%, PG 22.6%) had the following particle size distribution

| | |
|---|---|
| Average particle dia. $D_{50}$ | 10.36 μ* |
| 90% of the particle less than | 18.9 μ |
| 99% of the particle less than | 26.5 μ |

*μ micron

Non Aqueous Phase: Non aqueous blend of organic components was made by blending 24 kg of ceraphyl 230 (diisopropyl adipate) with 6 kg of DC 556, 3 kg of Silsoft PEDM; 3 kg of Dermol G-76 and 720 gm of Tween 80. The blend was mixed for 2 hrs. using an overhead agitator. The resultant blend had RI of 1.43995. The refractive index was measured using Leica Auto Abbe refractometer at a constant temperature of 21° C.

Suspension and Wet Milling: 8.3 kg of Reach AZP-908 PG powder was suspended in 8.5 kg of non aqueous organic solvent blend using an overhead mixer. This suspension was fed to Netzch media mill model #LMZ 0.5 UHMW which utilized 0.65 mm yitrium stabilized zirconium oxide media, at the end of four (4) passes thru the mill average particle size was less than 2 micron. Average particle size of the gel was 1.885μ and 90% of the product had particle size less than 8.7 micron.

EXAMPLE II 18 kg of basic aluminum sesquichloride solution (Al 11.79%, Cl 8.89%, Al:Cl atomic ratio 1.76) was mixed with 3 kg of USP grade propylene glycol and the solution was refluxed for 2 hrs., cooled to room temperature and spray dried to yield a white powder of Reach 301 PG (Al 21.3%, Cl 16.2%, PG=21.6%).

3.15 kg of Reach 301 PG powder was blended with 3.85 kg of the above non aqueous oil phase and the suspension was milled in the same manner as example I. The average particle size was 2.3μ with 90% of the particle below 3.7μ.

Reach AZP-908 PG gel of Example 1 and Reach 301 PG gel of Example 2 were formulated into solid (opaque) stick using the formulation shown in Table X.

TABLE X

Antiperspirant Stick Formulations

Stick Formulation

| Ingredients | % By Wt. |
|---|---|
| A. Octylodecanol (a) | 16.0 |
| B. C20–40 Pareth-10 (b) | 0.5 |
| C. C20–40 Pareth-40 (b) | 1.5 |
| D. C20–40 Alcohols (c) | 0.5 |
| E. Stearyl Alcohol (c) | 5.0 |
| F. Hydrogenated Castor Oil (d) | 2.0 |
| G. N-Acyl Glutamic Acid Diamide (e) | 2.0 |
| H. Di(hydrogenated) Tallow Phthalic Acid Amide (f) | 10.0 |
| I. Cyclomethicone (Pentamer) (g) | 34.5 |
| J. Phenyl Trimethicone (g) | 2.5 |
| K. Bentone Gel VS5/PC (h) | 1.0 |
| L. Reach AZP 908 SUF | 2.40 |
| M. Fragrance | |
| | 100.00 |

Procedure

1. Combine A, B, C, D, E and F and heat to 110° C. until clear.
2. Add G slowly and heat to 120° C. until clear. Use overhead mixer and mix well at each step.
3. Cool to 70° C. Add H slowly and mix until clear.
4. Separately combine I, J, and K. Mix until homogeneous. Heat to 65° C.–70° C.

TABLE X-continued

Antiperspirant Stick Formulations

5. Add step 4 to step 2 and mix well. Maintain 70° C.
6. Slowly add L, maintain 70° C., and mix well until homogeneous. (A portion of L can be premixed with step 2).
7. Cool to 58°–60° C., add M and mix well.
8. Pour into suitable containers.

(a) Henkel (Eutanol G)
(b) Pertrolite (Unithox 450 Ethoxylate; Unithox 480 Ethoxylate; Unilin 350 Alcohol)
(c) Protameen or Henkel
(d) Henkel (Cutina HR)
(e) Ajinomoto (GP-1 Gellant)
(f) Stepan (Stepan Tab-2)
(g) Dow Corning (DC 556 Fluid) or GE Silicones (SF 1202)
(h) Rheox The stick made from the active of Example 1 was evenly applied on a black (8×11) paper using three even strokes. The black paper was visually observed for any visible white residue and chromacity index (DC) which is a measure of whiteness, was determined using Macbeth Color Eye Model 2020 in reflectance mode. The chromacity index was 0.35. Visually no white residue was visible. White residue is visible when the chromacity index is greater than about 0.5. The process was repeated using the stick made from the active of example 2 and there was no visible white residue. Results clearly demonstrated that the novel antiperspirant composition of the invention can be formulated into highly efficacious non tacky, quick drying opaque stick with excellent sensory properties which leaves no visible white residue. While lower chromacities lower than 0.25 may be provided, from a practical and functional standpoint, a chromacity of between 0.3 and 0.4 is preferred.

Since the second step of the present invention requires suspending an antiperspirant/deodorant active into a non aqueous phase having controlled refractive index to enrobe the particles was thought that it may not be necessary to form an adduct if the average particle size was reduced to one micron or less. Another objective was to determine the results of using a randomly selected nonaqueous phase only on the basis of refractive index and its suitability for topical application.

Activated aluminum zirconium tetrachlorohydrex glycine complex (Reach AZP-908 SUF, a product of Reheis Inc.) was chosen as an active of choice for comparison with Example 1 (Al 14.9%, Zr 14.1%, Cl 17.9%, Glycine 11.8%).

Reach AZP-908 SUF powder was wet milled using Netzsch silicon carbide (nonmetal) Labstar zeta mill with a total of seven different nonaqeous phases and different nonaqeuous phases were prepared using different ingredients as shown by Table XII. In general, the selection criteria used for five nonaqueous phases were refractive index, ability to provide stearic structure, particle dispersant and surfactant for viscosity control. Two nonaqueous phases were selected to determine whether the use of single fluid like cyclomethicone (Example VI) or in combination with emollient (Example VII) would give an acceptable product or not. Refractive Index of nonaqueous phase was controlled between 1.40 and 1.44.

TABLE XII

Non Aqueous Phase Formulations

| | Example | | | | | | |
|---|---|---|---|---|---|---|---|
| | III | IV | V | VI | VII | VIII | IX |
| Ceraphyl 230 | 65.3 | | | | | | |
| DC-556 | 16.3 | | | | | | |
| Silsoft-PEDM | 8.2 | 10 | | | | 24.5 | |
| Dermol G-76 | 8.2 | | 32.9 | | | | |
| Silkflo 364-NF | | | | | 16.5 | | |
| Silicone Oil SF-1555 | | 29.6 | | | | | 30 |
| Cyclomethicone SF-1202 | | 59.4 | | 99 | 50 | 72.75 | 55 |
| Octyl Isononanoate | | | 32.9 | | 16.5 | | |
| PEG-14 Butyl Ether | | | 16.5 | | 8.2 | | 15 |
| Light Mineral Oil | | | 16.5 | | 8.2 | 1.9 | |
| Tween-80 | 2 | 1 | 1.2 | 1 | 0.60 | 1.1 | — |
| Lecithin | — | — | — | — | — | — | 0.25 |
| RI | 1.43940 | 1.42587 | 1.4449 1.42493 | 1.39830 | 1.42533 | 1.41772 | 1.42544 |

The mill size used for all the six experiments was LS1 with urethane shaft, silicon carbide chamber, 3.5 HP motor and the screen size was 0.4 mm. The media used was yitrium stablilized zirconia having 0.8 mm size. Void volume was 0.28 liter. The suspension was wet milled till the desired particle size was achieved. Typically it took 75 to 100 minutes depending upon the properties of the nonaqueous phase chosen. The resultant paste had an average particle size $D_{50}$ of about 1–1.2 micron and in most cases 99% of particles were less than 2 micron thus giving a very narrow particle size distribution as shown by Table XIII. Average antiperspirant concentration was in the range of 40–45%.

TABLE XIII

Particle Size Distribution

| Particle Size in Microns | Example | | | | | | |
|---|---|---|---|---|---|---|---|
| | III | IV | V | VI | VII | VIII | IX |
| 50% less than | 1.155 | 1.133 | 0.982 | 1.272 | 1.003 | 1.333 | 1.343 |
| 90% less than | 1.566 | 1.495 | 1.130 | 1.767 | 1.304 | 1.881 | 1.343 |
| 99% less than | 2.055 | 1.975 | 1.288 | 2.430 | 1.664 | 2.551 | 2.555 |
| Viscosity cps* | 29,450 | 38,000 | 9,900 | 27,750 | 27,000 | 36,200 | 22,000 |

*Viscosity was measured using Brookfield viscometer spindle # 6 at 20 RPM.

Using the formula and methodology described in Table IV hereinabove, antiperspirant sticks were prepared, using five pastes while maintaining active concentration at the same level 24%. Actual quantity of ingredients used are shown by Table XIV.

TABLE XIV

Antiperspirant Stick Formulations

| | Ingredients Examples | | | | |
|---|---|---|---|---|---|
| | Wt % III | Wt % IV | Wt % V | wt % VI | Wt % VII |
| (A) Octyldodecanol | 8 | 8 | 8 | 8 | 8 |
| (B) C20–40 Pareth 10 | 0.5 | 0.5 | 0.5 | 0.5 | 0.5 |
| (C) C20–40 Pareth 40 | 1.5 | 1.5 | 1.5 | 1.5 | 1.5 |
| (D) C20–40 Alcohol | 0.5 | 0.5 | 0.5 | 0.5 | 0.5 |
| (E) Stearyl Alcohol | 4 | 4 | 4 | 4 | 4 |
| (F) Hydrogenated Castor Oil | 2 | 2 | 2 | 2 | 2 |
| (G) N-Acyl Glutamic Acid Diamide | 2 | 2 | 2 | 2 | 2 |
| (H) Dihydrogenated Tallow Phosphate | 8 | 8 | 8 | 8 | 8 |
| (I) Cyclomethicone (SF-1202) | 22 | 37.6 | 21 | 48.7 | 35 |
| (J) Phenyl Trimethicone (DC-556) | 4.5 | — | — | — | — |
| (K) Ceraphyl-230 (DIPA) | 17.5 | — | — | — | — |
| (L) Silsoft PEDM | 2.25 | 2.8 | — | — | — |
| (M) Dermol G-76 | 2.25 | — | — | — | — |
| (N) Silicone Oil SF-1555 | — | 8.3 | — | — | — |
| (O) Silkflo 364 NF | — | — | 9.25 | — | 4.6 |

TABLE XIV-continued

Antiperspirant Stick Formulations

| Ingredients Examples | Wt % III | Wt % IV | Wt % V | wt % VI | Wt % VII |
|---|---|---|---|---|---|
| (P) Octyl Isononanoate | — | — | 9.25 | — | 4.6 |
| (Q) PEG-14 Butyl Ether | — | — | 4.6 | — | 2.25 |
| (R) Light Mineral Oil | — | — | 4.6 | — | 2.25 |
| (S) Bentone Gel VS51PC | 0.5 | 0.5 | 0.5 | 0.5 | 0.5 |
| (T) AZP-908 SUF | 24 | 24 | 24 | 24 | 24 |
| (U) Tween-80 | 0.5 | 0.3 | 0.3 | 0.3 | 0.3 |
| Chromacity Index | .34 | .39 | .33 | 1.18 | 1.12 |

All the sticks were tested for visual residue against black background.

Opaque sticks made from using antiperspirant gels of examples I, II, III, IV & V gave no visible white residue against black background and had chromacity index of less than 0.4. Example VI showed the most white residue even though the average particle size was less than 1.272μ. The chromacity index was 1.18. Thus, milling with cyclomethicone alone did not give an acceptable product. Examples seven showed white residue indicating the choice of ingredients for nonaqueous phase is a critical step and plays an important role in visibility of white residue. The results demonstrate that the novel product of this invention gives no visible white ugly residue when properly formulated into opaque sticks.

The invention has been described in terms of particular embodiments and blends of one or more of the various additives described herein. Various alternatives and substitutes therefore, may be employed as is known to those skilled in the art. It will be understood that the invention is not to be limited to the details described herein, unless so required by the scope of the appended claims.

What is claimed is:

1. An antiperspirant composition comprising:
 a) from about 5% to about 65% by weight of an antiperspirant from the group of activated and activated or unactivated antiperspirant compositions selected from;
 (I) those aluminum zirconium actives having the formula

$Al_nZr(OH)_{(3n+4-x)}Y_x(AA)q(R)p$ wherein "n" is from 2.0 to 10.0;
 wherein "x" is from 1.4 to 12.3, calculated from metal to anion ratio of from 0.9:1 to 2.1:1;
 wherein "Y" is Cl, Br, I and/or $NO_3$
 wherein "q" is from 0.5 to 3.0; AA is amino acid, and wherein "R" is an organic solvent having at least two carbon atoms and at least one hydroxy group and "p" has a value of from zero to 1.5;
 (II) those basic aluminum chlorides having the formula;

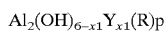

$Al_2(OH)_{6-x1}Y_{x1}(R)p$ wherein Y is Cl, Br, I and/or $NO_3$ and $x_l$ is greater than zero and less than or equal to six (i.e., $0 < x_1 \leq 6$); and
 wherein "R" is an organic solvent having at least two carbon atoms and at least one hydroxy group and "p" has a value of from zero to 1.5; and
 (III) those aluminum and aluminum-zirconium salts combined with zinc and/or tin having refractive index of antiperspirant powder from 1.40 to 1.58 and preferably low surface area to mass ratio; and
 b) a non-aqueous phase consisting of at least three components selected from nonpolar, nonwater miscible organic liquid capable of providing stearic space, polyesters and polyethers from fatty acids and alcohols; alkoxylated fatty esters of PEG and silicone copolyols and alkoxylated methyl glucoside; and
 c) wherein the chosen nonaqueous phase has a refractive index from 1.40 to 1.50 and the average particle size of the antiperspirant is less than 3 microns and the viscosity of the wet milled antiperspirant is less than 50,000 cps.

2. The composition of claim 1 wherein "n" in the aluminum zirconium actives formula is from about 3 to about 8.

3. The product of claim 1 wherein the antiperspirant composition is from about 20% to 40%.

4. The composition of claim 1 where antiperspirant actives have a surface area to mass ratio of about 0.2 m²/gm to about 1.0 m²/gm, a refractive index from of about 1.400 to about 1.5800 and a critical humidity of less than 20%.

5. The composition of claim 1 wherein q is zero and the average particle size of the powder is about 44 microns and critical humidity is less than 30%.

6. The composition of claim 5 where the activated antiperspirant composition has a surface area to mass ratio of about 0.4 m²/gm to about 3 m²/gm.

7. The composition of claim 1 wherein the nonaqueous phase is comprised of at least three components from a group consisting of linear and branched hydrocarbons, polyethers and polyesters, alcohols and fatty acids, alkoxylated fatty esters of PEG, and silicon copolyols and alkoxylated methyl glucoside and have a refractive index in the range of about 1.400 to 1.500.

8. The composition of claim 1 wherein the three components of the nonaqueous phase are chosen such that the nonaqueous phase has RI from 1.40 to 1.45 and are selected from the group consisting of: diisopropyl adipate, glycereth-7-benzoate, phenyl trimethicone, phenyl ethyl dimethicone, PPG-14-butyl ether, PPG-15-stearyl ether benzoate, 2-phenyl propyl terminate silicone oil, lecithin, POE (20) sorbitan mono oleate, POE (20) sorbitan mono laurate, POE (20) sorbitan mono stearate, POE (20) sorbitan mono palamitate, alkyl polyglycoside, dimethicone, dimethicone copolyols, light mineral oil and ethyl hexyl glycerin.

9. The composition of claim 1 wherein an inorganic-organic adduct is formed and the RI of the antiperspirant active is about 1.490 to 1.550 and the organic solvent is selected from the group consisting of: propylene glycol, dipropylene glycol, tripropylene glycol, 2-methoxy ethanol, 1-methoxy 2-propanol, 2-ethoxy ethanol, 3-methoxy butanol, 1,4-butanediol, 2-methyl 1,3-propanediol, glycerin and diglycerol.

10. The composition of claim 5 wherein the average particle size is less than 5 microns.

11. The composition of claim 5 wherein the average particle size is less than three micron and viscosity of the antiperspirant gel is less than 40,000 cps.

12. The composition of claim 1 wherein the antiperspirant salt is characterized in having a critical humidity from about 6% to 30%.

13. The composition of claim 1 wherein the antiperspirant active materials are covered by FDA OTC Tentative Final Monograph as Category I.

14. The composition of claim 1 wherein the antiperspirant active is an activated or unactivated aluminum zirconium tetrachlorohydrex glycine propylene glycol complex in the form of macrospherical powder or spray dried powder or superultrafine powder.

15. The composition of claim 1 wherein the antiperspirant active is a propylene glycol adduct of activated or unactivated aluminum chlorohydrate.

16. The composition of claim 1 wherein the antiperspirant active is a propylene glycol adduct of aluminum sesquichlorohydrate.

17. The composition of claim 1 wherein the antiperspirant salts are zirconium compounds of the formula $$ZrO(OH)_{2-ab}X_6$$

wherein X is a member selected from the group consisting of halide, nitrate, pechlorate, carbonate or sulfate; b varies from 0.5 to 2; a is the valence of X; (2–ab) is greater than or equal to zero.

18. The composition of claim 1 wherein a salt selected from zinc, tin and mixtures thereof is added.

19. A method for preparing an antiperspirant suspension having an antiperspirant active concentration of about 5% to 65% by weight comprising:
a) suspending an antiperspirant salt represented by formulas I and II of claim 1 in a nonaqueous phase consisting of at least three components selected from nonpolar, nonwater miscible organic liquid comprising linear and branched hydrocarbons and polyethers from fatty acids and alcohols, alkoxylated fatty esters of PEG and silicon polyols and alkoxylated methyl glucoside wherein the chosen nonaqueous phase has a refractive index of about 1.40 to 1.50; and
b) milling the suspension to achieve an average particle size of less than 3 micron and at a temperature less than 65° C.

20. The method of claim 19 wherein the suspension is wet milled using a Netzsch media mill using grinding media which does not contaminate the product.

21. The method of claim 19 wherein the suspension is processed in a spinning tube in tube device.

22. The method of claim 19 wherein the nonaqueous phase comprises about 65% diisopropyl adipate, about 16% phenyl trimethicone, phenyl ethyl dimethicone, glycereth-7-benzoate, and about 2% POE (20) sorbitan mono oleate and has a refractive index of about 1.43 to 1.45 and antiperspirant activated or unactivated aluminum or aluminum zirconium glycine complexes as represented by formula 1 and 2 of claim 1 and adducts thereof with organic solvent.

23. The method of claim 19 wherein the nonaqueous phase comprises about 40% of a phenyl substituted silicone oil, about 60% of cyclomethicone, about 2% polyoxyethylene sorbitan monooleate and encompassed within the product categories covered by the FDA OTC Tentative Final Monograph as Category I and having average particle size of less than about 44$\mu$ to give a novel antiperspirant with an average particle size less than about 1.5 microns, a refractive index of less than about 1.55 and a viscosity of less than 40,000 cps.

24. The method of claim 19 wherein the three components of the nonaqueous liquid vehicle are chosen such that the nonaqueous phase has RI from 1.41 to 1.45 and are selected from the group consisting of: diisopropyl adipate, glycereth-7-benzoate, phenyl trimethicone, phenyl ethyl dimethicone, PPG-14-butyl ether, PPG-15-stearyl ether benzoate, 2-phenyl propyl terminate silicone oil, lecithin, POE 20) sorbitan mono oleate, POE (20) sorbitan mono lamrate, POE (20) sorbitan mono stearate, POE (20) sorbitan mono palamitate, alkyl polyglycoside, dimethicone, dimethicone copolyols, and light mineral oil.

25. The method of claim 19 where the antiperspirant suspension incorporates ingredients selected from one or more suitable antibacterials fragrances and color.

26. The method of claim 19 wherein the antiperspirant is co-dried with an antibacterial deodorant additive.

27. The method of claim 26 where the antibacterial is 2,4,4'-trichloro-2'-hydroxydiphenyl ether.

28. The method of claim 25 where the antibacterial is ethyl hexyl glycerin.

29. An anhydrous personal care product comprising 15–40% of the product according to claim 1 in the form of a stick comprising 20–80% of a constituent selected from the group consisting of cyclomethicone, 5–8% wax gelling agent, 0.5–10% surfactant, 0–50% emollients and 0.25–3% fragrance.

30. An anhydrous personal care product which is a soft solid comprising 15–40% of the product of claim 1; 20–80% of a member selected from the group consisting of cyclomethicone and isoparaffin; 5–80% wax gelling agent; 0–20% surfactant; 0–50% emollient; 0–3% fragrance; 0–10% clay; and 0–60% inert filler.

31. An anhydrous personal care product which is a roll-on comprising 20–90% cyclomethicone; 0–20% dimethicone having a viscosity of up to 350 centistokes; 0–10% quaternium-18 hectorite; 15–40% of product of claim 1 and 0–3% fragrance.

32. An anhydrous personal care product which is an aerosol comprising 5–30% cyclomethicone and/or isoparaffin; 0–20% dimethicone having a viscosity of up to 350 centistokes; 0–10% quaternium-18 hectorite; 50–80% propellant; and 0–3% fragrance and 10–15% of product of claim 1.

* * * * *